United States Patent [19]
Asher et al.

[11] Patent Number: 5,312,404
[45] Date of Patent: May 17, 1994

[54] SPINAL COLUMN RETAINING APPARATUS

[75] Inventors: Marc A. Asher, Leawood, Kans.;
Walter E. Stripggen, Golden, Colo.;
Charles F. Heinig, Ware Neck, Va.;
William L. Carson, Columbia, Mo.

[73] Assignee: AcroMed Corporation, Cleveland, Ohio

[21] Appl. No.: 839,243

[22] Filed: Feb. 20, 1992

Related U.S. Application Data
[63] Continuation-in-part of Ser. No. 557,587, Jul. 24, 1990, Pat. No. 5,129,900.

[51] Int. Cl.⁵ .............................................. A61F 5/00
[52] U.S. Cl. ........................................ 606/61; 606/72; 606/73
[58] Field of Search .................... 606/61, 62, 63, 64, 606/72, 73

[56] References Cited
U.S. PATENT DOCUMENTS
4,433,676 2/1984 BoBechko .......................... 606/61
5,002,542 3/1991 Frigg ................................... 606/61
5,133,717 7/1992 Chopin ............................... 606/73

Primary Examiner—Richard J. Apley
Assistant Examiner—Lynne A. Reichard
Attorney, Agent, or Firm—Tarolli, Sundheim & Covell

[57] ABSTRACT

An apparatus is provided to retain elements of the spine or pelvis or both in a desired spatial relationship. A plurality of fasteners are connected with a plurality of the elements. A longitudinal member is connected with that fasteners by a plurality of connector members. The longitudinal members and fasteners are movable relative to each other to adjust the distance between the longitudinal member and fasteners to thereby obtain the desired spatial relationship. Clamps are engaged to hold the longitudinal member, fasteners, and connector members against relative movement. To provide for adjustability, oblong openings are formed in the connector members. The fasteners have a plurality of tapered washers to create variable angles between the axis of the fastener and the axis of the oblong opening.

5 Claims, 5 Drawing Sheets

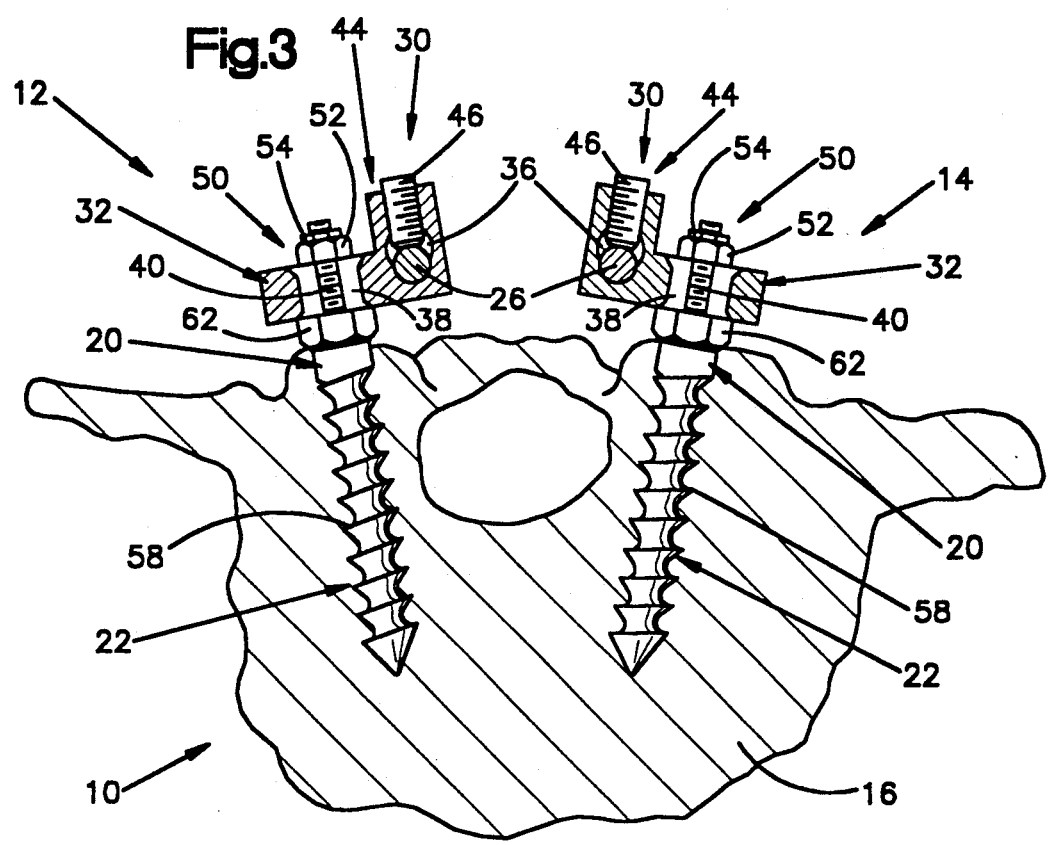
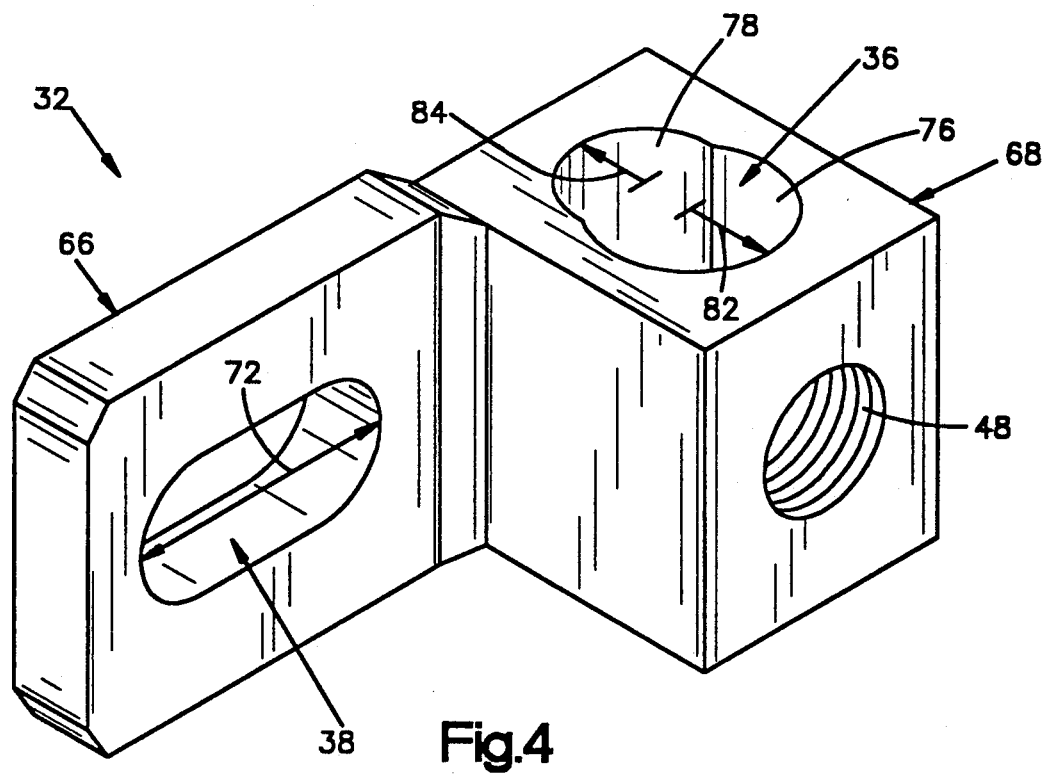

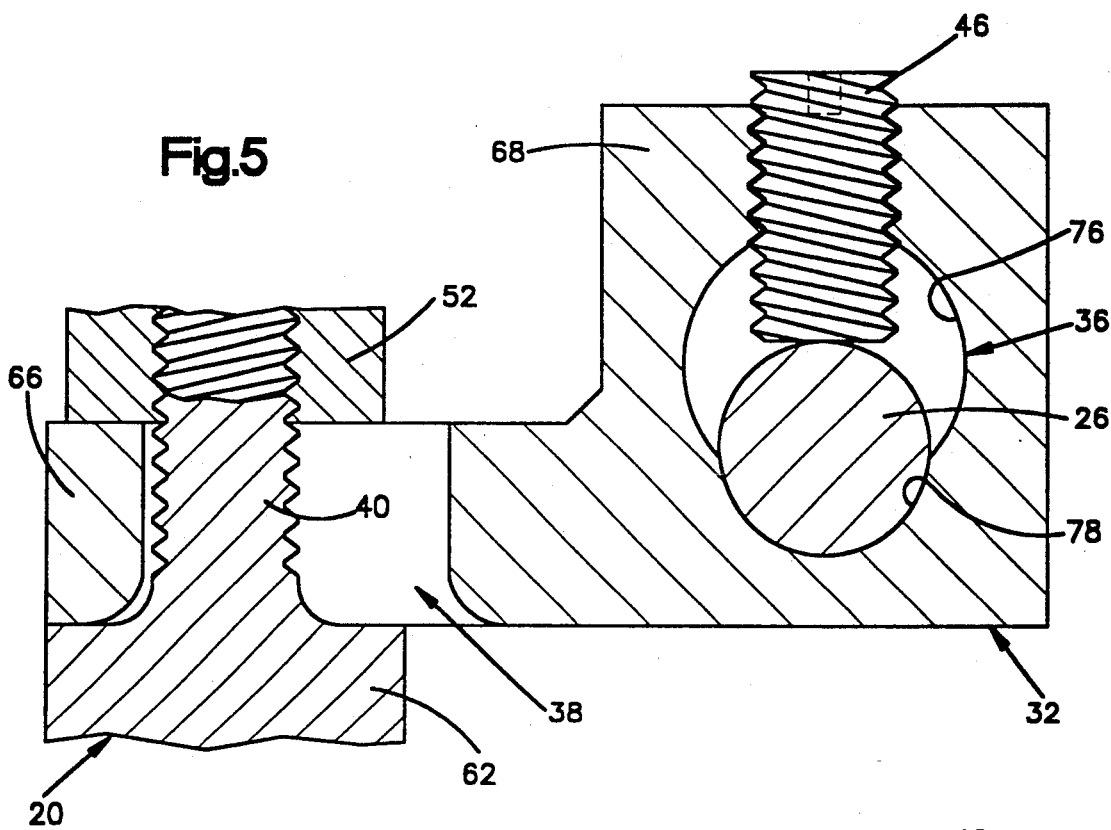
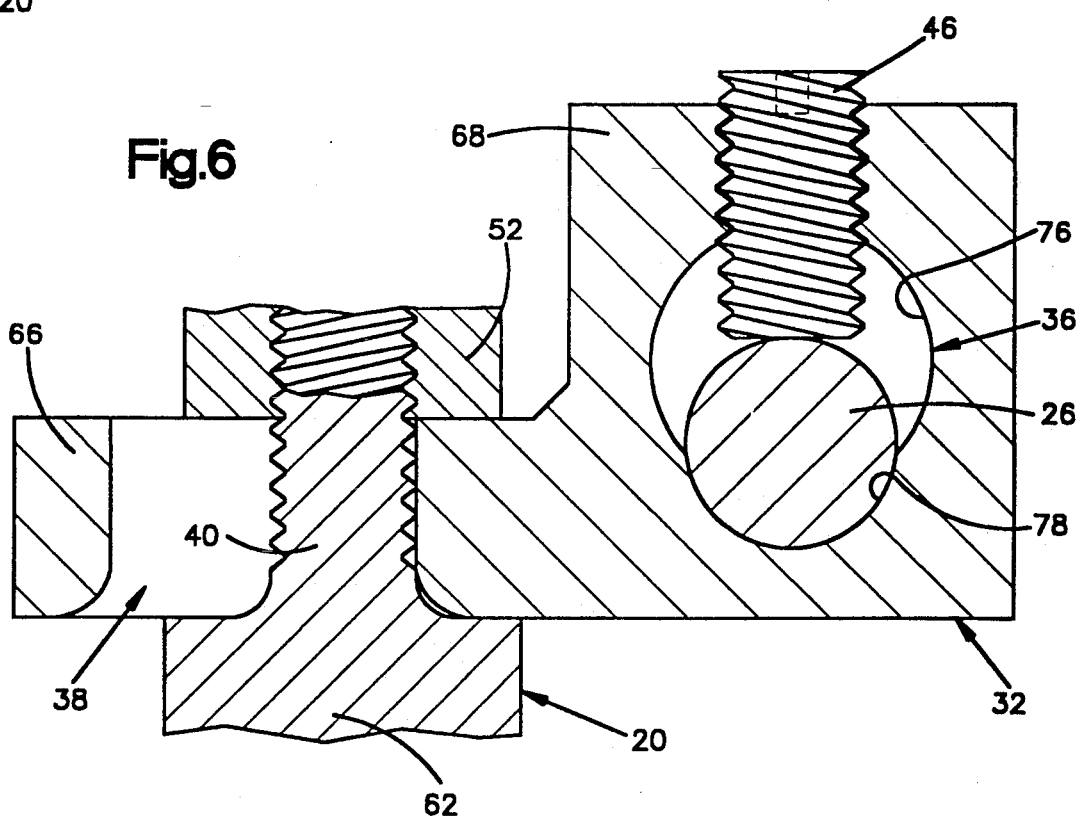

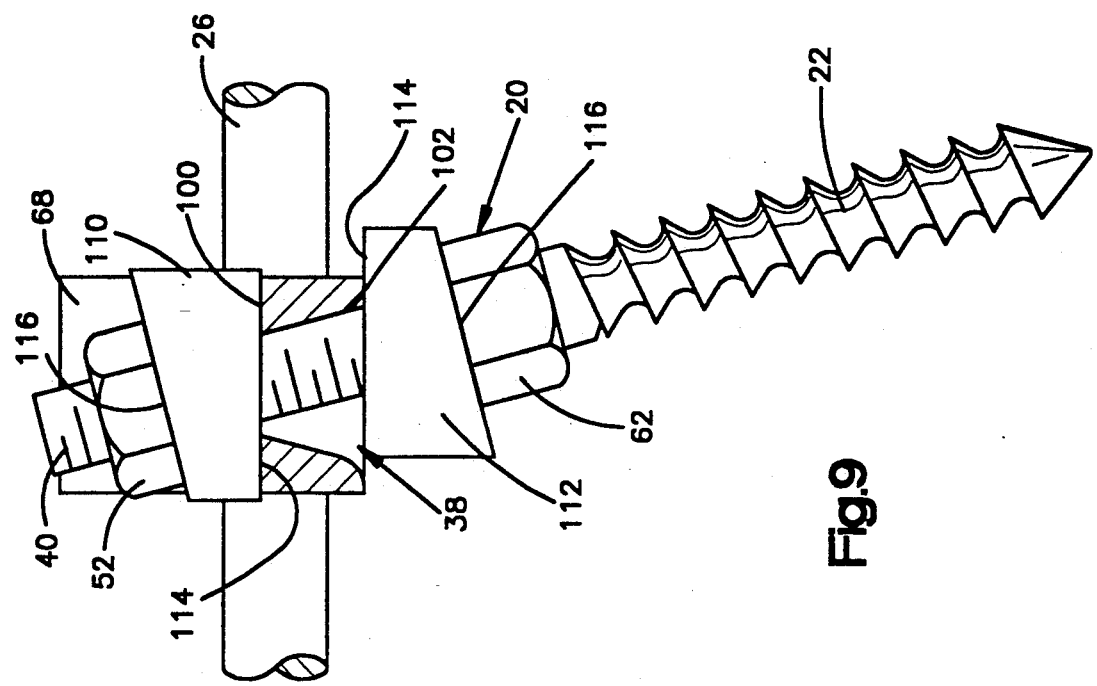
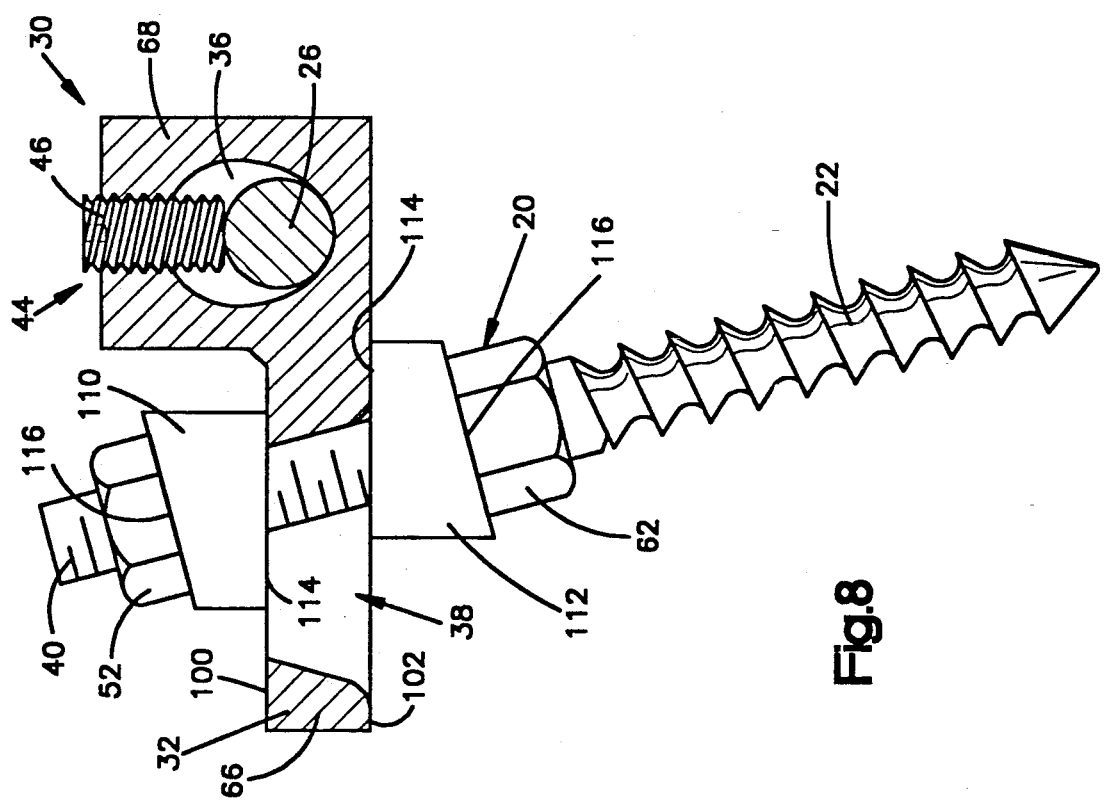

SPINAL COLUMN RETAINING APPARATUS

This application is a continuation-in-part of application Ser. No. 07/557,587, filed Jul. 24 1990, now U.S. Pat. No. 5,129,900 entitled "Spinal Column Retaining Method and Apparatus", which is assigned to the assignee of the present application.

BACKGROUND OF THE INVENTION

The present invention relates to a method and apparatus which is used to retain spinal and/or pelvic elements, such as vertebrae for example, in a desired spatial relationship.

A known apparatus for retaining vertebrae in a desired spatial relationship is disclosed in U.S. Pat. No. 4,648,388. The apparatus includes a plurality of threaded fasteners which are connected with vertebrae of a human spinal column. Retaining rods are bent to a configuration which is a function of the desired spatial relationship between vertebrae of the spinal column. After a rod has been bent to the desired configuration, it is inserted into clamps connected with the fasteners. The clamps are then engaged to hold the vertebrae against movement relative to the rod. Other known apparatus for retaining vertebrae in a desired spatial relationship are disclosed in U.S. Pat. Nos. 4,611,581; 4,655,199; and 4,887,595.

With this known apparatus, once the threaded fasteners or bone screws have been connected with the vertebrae, it is difficult to adjust the position of a retaining rod relative to the fasteners. This is because once the fasteners or bone screws have been connected with the vertebrae, each of the fasteners remains stationary relative to the vertebra with which it is connected. The clamps which interconnect the retainer rod and the fasteners cannot be adjusted to change the spatial relationship between the fasteners and the retainer rod.

SUMMARY OF THE INVENTION

The present invention provides a new and improved apparatus and method for us in retaining spinal and/or pelvic elements, such as vertebrae, in a desired spatial relationship. The apparatus includes a fastener having a threaded end portion which engages an element, such as a vertebra, in the spinal column. A connector assembly interconnects the fastener and a longitudinal member, such as a rod, which extends substantially parallel to the axis of the spine. The connector assembly is adjustable to enable the distance between the longitudinal member and the fastener to be varied while the fastener remains stationary relative to the element, such as a vertebra to which it is connected.

To accommodate the adjustment between the longitudinal member and fastener, an oblong opening is formed in a connector member which interconnects the longitudinal member and fastener. Thus, after the connector member has been placed in engagement with both the longitudinal member and the fastener, the longitudinal member and fastener can be moved relative to each other while the connector member is maintained in engagement with both the longitudinal member and the fastener. In one specific embodiment of the invention, the oblong opening which accommodates temporary relative movement between the longitudinal member and fastener is engaged by the fastener. Therefore, the connector member and longitudinal member can be moved together relative to the fastener. If desired, to obtain the optimal surgical correction of the spine in all three planes, the positions of the vertebrae can be readily adjusted relative to each other by rotating the longitudinal member relative to the connector members with some of the connector members disposed in relatively loose engagement with the longitudinal member and fasteners and one or more connector members in relatively tight engagement with a fastener or fasteners. This makes it possible for example to vary or change both the radius and the apex of a coronal plane spine curve, which is by definition abnormal, as the curve is being transposed into a normal sagittal plane curve. After the adjustment, the fasteners are tightened to prevent relative movement of the longitudinal member and the fasteners.

In another embodiment of the present invention the oblong opening tapers from one side of the connector member to the other side of the connector member. A pair of identical tapered washers engage on opposite sides of the connector member. Each of the washers has a first side surface and a second side surface extending at an angle to the first side surface. The tapered opening and the tapered washers enable the fastener to be positioned with the axis of the fastener at an angle to the longitudinal axis of the oblong opening. The angle between the axis of the fastener and the longitudinal axis of the oblong opening can be changed by replacing the washers with washers that taper at a different angle.

BRIEF DESCRIPTION OF THE DRAWINGS

The foregoing and other features of the invention will become more apparent upon a consideration of the following description taken in connection with the accompany drawings, wherein:

FIG. 3 is a sectional view, taken generally along the line 3—3 of FIG. 1, illustrating the manner in which fasteners are used to connect the retainer assemblies with a vertebra;

FIG. 4 is an enlarged pictorial illustration of a connector member used in a retainer assembly of FIG. 3;

FIG. 5 is an enlarged sectional view illustrating the manner in which the connector member interconnects a retainer rod and a fastener when the distance between the retainer rod and fastener is relatively large;

FIG. 6 is a fragmentary sectional view, generally similar to FIG. 5, illustrating the manner in which a connector member interconnects the retainer rod and fastener when the distance between the retainer rod and fastener is relatively small;

FIG. 8 is an enlarged sectional view illustrating the manner in which a fastener can be positioned relative to the connector member of FIG. 7; and FIG. 9 is an enlarged sectional view illustrating another manner in which a fastener can be positioned relative to the connector member of FIG. 7.

DESCRIPTION OF SPECIFIC PREFERRED EMBODIMENTS OF THE INVENTION

General Description

Figure 1:
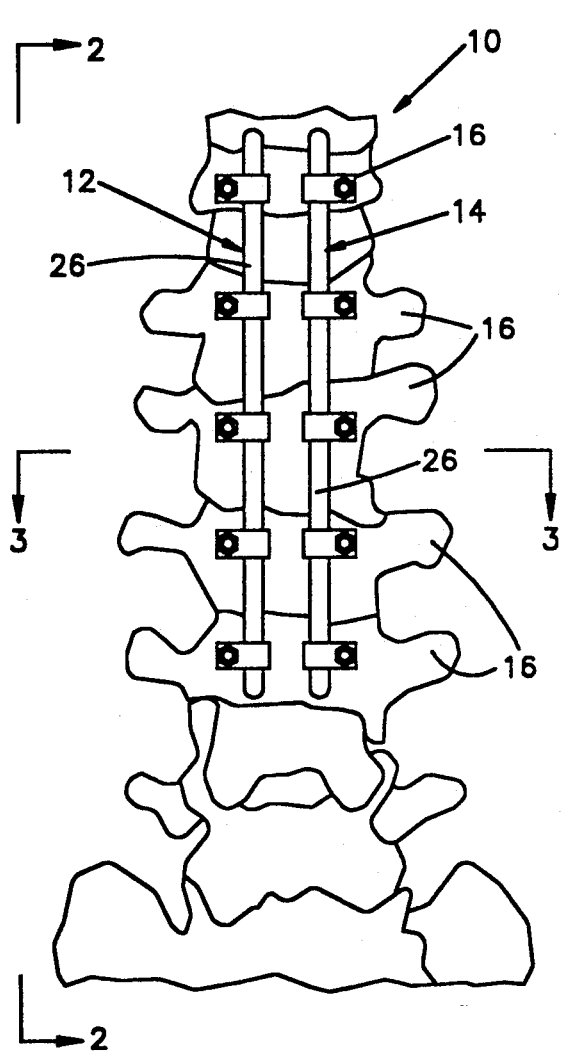
FIG. 1 is a dorsal view of a portion of a spinal column with retainer assemblies constructed and installed in accordance with the present invention to maintain a desired spatial relationship between vertebrae of the spinal column.
Figure 2:
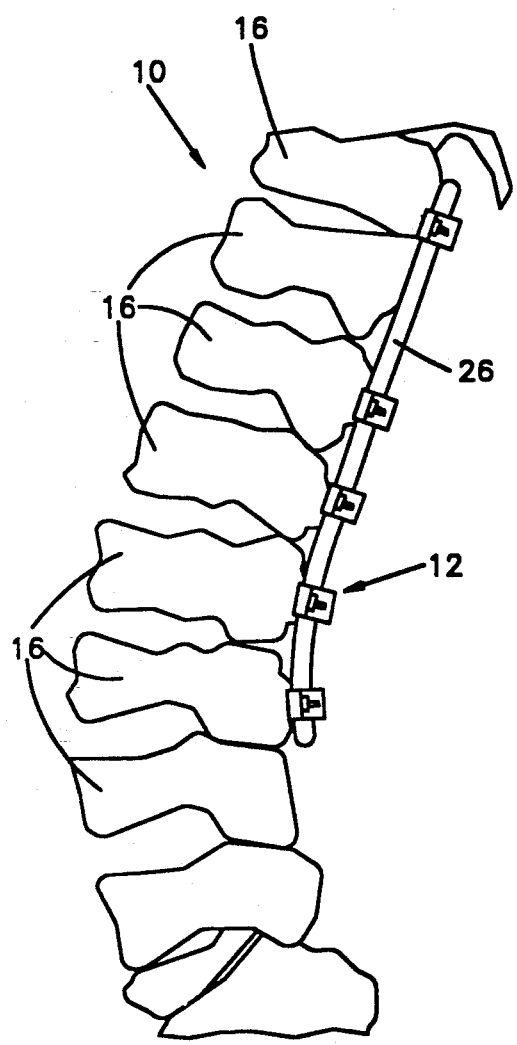
FIG. 2 is a sagittal view of the spinal column of FIG. 1, further illustrating the manner in which vertebrae of the spinal column are held in the desired spatial relationship.

A human spinal column 10 to which a pair of retainer assemblies 12 and 14 are connected is illustrated in FIGS. 1 and 2. The retainer assemblies 12 and 14 retain portions of the spinal column, that is vertebrae 16, in a desired spatial relationship relative to each other.

The retainer assemblies 12 and 14 have the same construction and include fasteners 20 (FIG. 3) made of a biocompatible material, such as stainless steel. The fasteners 20 have threaded inner end portions 22 which engage the vertebrae 16 to fixedly mount the fasteners in the vertebrae. Although only a pair of fasteners 20 have been shown in FIG. 3, it should be understood that there are usually more than that and in FIGS. 1 and 2 four pairs of fasteners 20 connected with four adjacent vertebrae 16 of the spinal column 10 are shown.

Each of the retainer assemblies 12 and 14 includes a longitudinal member such as the depicted cylindrical rod 26 which extends along the spinal column. The rod is made of a biocompatible material such as stainless steel. Each of the rods 26 has a length which is at least sufficient to enable the rod to span at least two of the vertebrae 16. In the embodiment of the invention illustrated in FIGS. 1 and 2, the rods 26 span six vertebrae 16. Of course, the length of the rods in any particular installation will depend upon the condition to be corrected and the number of vertebrae 16 to be held in a desired spatial relationship relative to each other by the retainer assemblies 12 and 14. The rods 26 are bent to conform to a desired curvature of the spinal column 10 in all or any of the three possible anatomic planes.

Connector assemblies 30 interconnect the rods 26 and the fasteners 20 (FIG. 3). Each of the connector assemblies 30 includes a connector member 32 (FIGS. 3 and 4). Each of the connector members 32 is provided with a first opening 36 through which the rod 26 extends. Each of the connector members 32 has a second opening 38 through which an outer end portion 40 of the fastener 22 extends.

Rod clamps 44 (FIG. 3) hold the rods 26 against movement relative to the connector members 32. The rod clamps 44 include set screws 46. The set screws 46 engage internally threaded openings 48 (FIG. 4) in the connector members 32.

Mounting clamps 50 (FIG. 3) hold the connector members 32 against movement relative to the fasteners 20. The mounting clamps 50 include clamp nuts 52 which engage relatively fine threads on the outer end portions 40 of the fasteners 20. Lock nuts 54 hold the clamp nuts 52 in place on the fasteners 20. The lock nuts 54 may be omitted if desired.

In accordance with one of the features of the invention, the distance between the rods 26 and the fasteners 20 can be varied while the rods 26 and fasteners are connected with the connector members 32 and while the fasteners remain stationary relative to the vertebrae 16. This enables the position of each of the rods 26 to be adjusted relative to each of the fasteners 20 after the fastener has been mounted in a vertebra. Therefore, compensation can be made for a slight misalignment of one or more of the fasteners 20 relative to a vertebra. In addition, the ability to adjust the distance between the fasteners 20 and the rods 26 enables one or more of the vertebrae to be moved relative to the adjacent vertebrae to obtain a desired spatial relationship between the vertebrae.

To enable temporary relative movement to occur between the rods 26 and fasteners 20, the openings 38 in the connector members 32 have an oblong configuration (FIG. 4). Therefore, a vertebra 16 (FIG. 3) engaged by a fastener 20 can be moved either toward or away from a rod 26 which is being held substantially stationary. Similarly, a rod 26 can be moved either toward or away from a fastener 20 which is being held stationary. Of course, the rod 26 and fastener 20 could both be moved relative to each other to obtain the desired spatial relationship. Once the desired spatial relationship has been obtained, the rod clamp 44 and mounting clamp 50 are tightened to hold the rod 26 and fastener 20 against movement relative to each other.

In the illustrated embodiment of the invention, the fastener 20 extends through an oblong opening 38 in the connector member 32. This enables relative movement to occur between the fastener 20 and connector member 32 as the rod 26 and fastener are moved relative to each other.

Fastener

The fastener 20 is formed from biocompatible material. The inner end portion 22 (FIG. 3) of the fastener 20 has a coarse helical thread convolution 58 which engages the bone of a vertebra 16. In one specific embodiment of the invention, the coarse thread convolution 58 is a buttress-type thread with an outside diameter of approximately 0.25 inches and a pitch of ten threads per inch. The outside diameter and the length of the threaded portion which engages the bone of vertebrae 16 may vary to safely accommodate the biological variability between vertebrae 16 of different individuals.

The outer end portion 40 of the one piece fastener 20 is provided with a relatively fine thread which engages an internal thread convolution on the clamp nut 52. In one specific embodiment of the invention, the outer end portion 40 had an outside diameter of approximately 0.19 inches. Wrenching flats (not shown) are provided on the outermost end of the outer end portion 40 of the fastener 20. Torque is applied to these wrenching flats to turn the relatively coarse helical thread convolution 58 into the bone of a vertebra 16. Once the fastener 20 has been connected with the vertebra and the rod 26 and fastener clamped in the desired spatial relationship, the outermost end portion of the fastener is cut away to minimize the overall length of the fastener. Of course, if desired, the outwardly projecting portion of the fastener could be left in place along with the wrenching flats for adjustment or removal purposes.

An enlarged intermediate portion 62 is provided between inner end portion 22 and outer end portion 40 of the fastener 20. The intermediate portion 62 is provided with wrenching flats which can be engaged to hold the fastener 20 against rotation when the clamp nut 52 is tightened. In addition, the intermediate portion 62 of the fastener has a flat outer side surface which abuttingly engages the connector member 32. When the clamp nut 52 is tightened, the connector member is securely gripped between the clamp nut and the enlarged intermediate portion of the fastener 20.

Although it is contemplated that the fastener 20 could have many different constructions, it is preferred to construct the fastener 20 in accordance with U.S. Pat. No. 4,854,311, issued Aug. 8, 1989 and entitled "Bone Screw". Thus, the fastener 20 has the same construction and cooperates with a vertebra 16 in the same manner as disclosed in the aforementioned U.S. patent.

First Embodiment of the Connector Member

The connector member 32 (FIG. 4) is formed from one piece of biocompatible material, such as stainless steel. The connector member 32 has a generally rectangular mounting section 66 which engages a fastener 20. In addition, the connector member 32 has a rectangular block section 68 which is integrally formed with the mounting section 66 and projects from the mounting section. The block section 68 engages a rod 26.

The oblong opening 38 is formed in the mounting section 66. The oblong opening 38 has a length, indicated by the arrow 72 in FIG. 4, which is sufficient to enable the connector member 32 to be moved through a substantial distance relative to the fastener 20. In one specific embodiment of the invention, the length 72 of the opening 38 was twice as great as the diameter of the outer end portion 40 of the fastener 20. In this particular embodiment of the invention, the length 72 of the opening exceeded the diameter of the outer end portion 40 of the fastener 20 by amount sufficient to enable the connector member 32 to be moved through a range of distance relative to the fastener 20 which was greater than one-half of the diameter or thickness of the rod 26. Thus, the length 72 of the opening 38 exceeds the sum of the diameter of the outer end portion 40 of the fastener 20 plus one-half of the diameter of the rod 26.

In this specific embodiment of the invention, the oblong opening 38 had a length 72 of 0.375 inches, the outer end portion 40 of the fastener had a diameter of 0.19 inches and the rod 26 had a diameter of 0.25 inches. In this embodiment of the invention, the length 72 of the opening 38 exceeds the sum of the outside diameter of the outer end portion 40 of the fastener 20 (0.19 inches) plus one-half of the diameter of the rod 26 (0.125 inches) by 0.065 inches. It should be understood that the foregoing specific dimensions for the slot 38, outer end portion 40 of the fastener 20, and rod 26 have been set forth herein merely for purposes of clarity of illustration. It is contemplated that the outer end portion 40 of the fastener 20, the oblong opening 38 and/or the rod 26 will be constructed with different dimensions in different embodiments of the invention. Further, the distance from the rectangular block section 68 and the oblong opening 38 may be varied. Also, the width of such an extended portion between the rectangular mounting section 66 and the rectangular block section 68 may be different than either the rectangular mounting section 66 or the rectangular block section 68.

The rectangular block section 68 (FIG. 4) of the connector member 32 projects outwardly from the mounting section 66 and receives the rod 26. Thus, the block section 68 is provided with an opening 36 through which the rod extends. The opening 36 in the mounting section 68 could be provided with a generally circular configuration if desired. However, in the embodiment of the invention illustrated herein, the opening 36 has a generally oval configuration.

The opening 36 includes a relatively large radius outer portion 76 and a relatively small radius inner portion 78. The large radius outer portion 76 has a radius which exceeds the radius of the rod 26. This enables the connector member 32 to be freely moved axially along the rod 26 to enable the connector member 32 to be accurately located relative to the fastener 20. The small radius section 78 of the generally oval opening 36 has a radius which is preferably slightly less than the radius of the rod 26. Therefore, when the clamp screw 46 is tightened to press the rod 26 into the inner portion 78 of the opening 36, in the manner shown in FIG. 3, the rod 26 is firmly and accurately gripped between the clamp screw 46 and the connector member 32.

In one specific embodiment of the invention, a relatively large upper portion 76 has a radius, indicated by the arrow 82 in FIG. 4, of approximately 0.115 inches or a diameter of 0.23 inches. The inner portion 78 of the opening 36 has a radius, indicated by the arrow 84 in FIG. 4, of approximately 0.099 inches or a diameter of 0.188 inches. In this particular embodiment of the invention, the rod 26 also has a diameter of 0.188 inches.

It should be understood that the foregoing specific dimensions for the portions 76 and 78 of the opening 36, the block section 68, and the rod 26 have been set forth herein only for purposes of clarity of description. It is contemplated that the opening 36 and rod 26 could have different dimensions if desired. In fact, it is contemplated that the opening 36 could be constructed with a substantially different configuration than the configuration illustrated in FIG. 4. In addition, the block section 68 may have a different shape to prevent interference with anatomic structures.

Second Embodiment of the Connector Member

Figure 7:
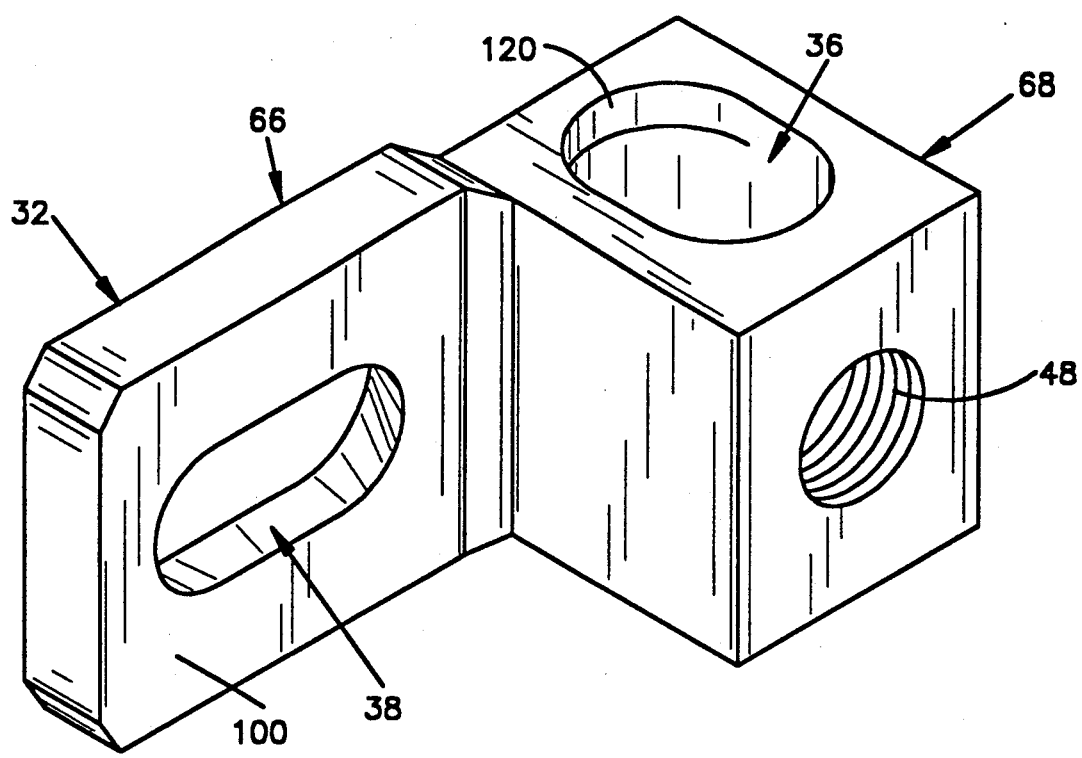
FIG. 7 is an enlarged pictorial illustration of a second embodiment of a connector member.

In another embodiment of the connector member 32, illustrated in FIGS. 7-9, the oblong opening 38 tapers to enable the axis of the fastener 20 to be positioned at an angle to the longitudinal axis of the oblong opening. The oblong opening 38 tapers from a first side 100 of the mounting section 66 to a second side 102 of the mounting section (FIGS. 8 and 9). The oblong opening 38 tapers from a relatively small opening in the first side 100 to a relatively large opening in the second side 102.

The outer end portion 40 of the fastener 20 extends through a pair of identical tapered washers 110 and 112. The tapered washer 110 engage the first side 100 of the mounting section 66 and the clamp nut 52. The tapered washer 112 engage the second side 102 of the mounting section 66 and the intermediate portion 62 of the fastener 20. Thus, the mounting section is clamped between the washers 110 and 112.

Each of the washers 110 and 112 includes a first side surface 114 and a second side surface 116 extending at an angle to the first side surface. The second side surface 116 extends at an angle of up to 15° to the first side surface 114. It is contemplated that the angle between the first and second side surfaces 114 and 116 may be of any value depending on the desired angle between the axis of the fastener 20 and the longitudinal axis of the oblong opening 38.

The axis of the fastener 20 can be positioned relative to the connector member 32 in a number of different manners. In FIG. 8 the axis of the fastener 20 extends so that the inner end portion 22 of the fastener is located beneath the rod 26. In FIG. 9 the axis of the fastener 20 extends so that the inner end portion 22 is not located beneath the connector member 32.

The opening 36 in the second embodiment of the connector member 32 includes a pair of axially spaced arcuate surfaces 120, one of which is illustrated in FIG. 7. The pair of axially spaced arcuate surfaces 120 engage portions of the rod 26 at axially spaced locations. Reference is hereby made to U.S. Pat. No. 5,024,213 to Asher et al. and assigned to the same assignee as the present invention. U.S. Pat. No. 5,024,213 describes the arcuate surfaces and their function in greater detail.

Mounting of Retainer Assembly

The retainer assemblies 12 and 14 can be mounted on a human spinal column 10 in any one of several different ways. Although a description of only two different ways of mounting the retainer assemblies 12 and 14 on the spinal column 10 will be set forth herein, it should be understood that the particular procedure used to mount the retainer assemblies 12 and 14 on a spinal column can be varied to suit the condition of the spinal column, the location of the retainer assemblies along the spinal column, and the extent to which vertebrae 16 are to be moved relative to each other to obtain the desired spatial relationship between the vertebrae. Therefore, the following description of methods of mounting the retainer assemblies 12 and 14 should merely be considered as exemplary of two specific preferred mounting procedures.

When the retainer assemblies 12 and 14 are to be mounted on a spinal column 10 (FIGS. 1 and 2), a plurality of fasteners 20 (FIG. 3) are connected to the vertebrae 16. This is accomplished by turning or screwing the coarse thread convolutions 58 on the inner end portions of the fasteners 20 into the vertebrae. Torque is applied to the fasteners 20 at wrenching flats (not shown) at the outer ends of the fasteners. Of course, if desired, torque could be applied to the wrenching flats at the intermediate portions 62 of the fasteners. Once the helical thread convolution 58 on the inner end portion of a fastener 20 has been turned into the bony material of a vertebra 16, in the manner shown in FIG. 3, the fastener 20 is fixedly connected with the vertebra 16 and does not move relative to the vertebra.

After the rods 26 have been bent to the desired configuration in the necessary anatomic planes, a plurality of connector members 32 are placed on each of the rods by inserting the rods through the openings 36 in the block sections 68 of the connector members. At this time, if the first embodiment of the connector members 32 are being used, the rods 26 will extend through the relatively large radius outer portions 76 of the openings 36 to enable the connector members to be freely moved axially along the rods 26. Once a number of connector members 32 corresponding to the number of vertebra to which the rods 26 are to be connected have been positioned on each of the rods, the rods are positioned along the spinal column 10 with the longitudinal central axes of the rods extending generally parallel to the longitudinal central axis of the spinal column. Thus, the rods 26 are generally located in the position shown in FIG. 1 relative to the spinal column 10.

Once the rods 26 have been positioned relative to the spinal column 10, the oblong openings 38 in the connector members 32 are positioned in engagement with the outer end portions 40 of the fasteners 20. As this is done, the clamp nuts 52 are loosely threaded onto the outer end portions of the fasteners 20 to prevent disengagement of the connector members 32 from the outer end portions of the fasteners. If the second embodiment of the connector members 32 are being used the second tapered washers 112 are placed on the outer end portions 40 of the fasteners 20 prior to positioning the oblong openings 38 in engagement with the outer end portions 40 of the fasteners 20. The first tapered washers 110 are placed on the outer end portions 40 before the clamp nuts 52 ar loosely threaded onto the outer end portions.

The spatial relationship between each of the rods 26 and the associated fasteners 20 is then adjusted while maintaining each of the fasteners stationary relative to the vertebra 16 which it engages. This adjustment can be accomplished by pulling the rod 26 and connector member 32 toward or away from a fastener 20. It could also be accomplished by pulling a fastener 20 and vertebra 16 toward or away from a rod 26. Of course, the rod 26 and fastener 20 could both be simultaneously moved relative to each other to obtain the desired spatial relationship between the rod and fastener.

Due to the presence of the oblong openings 38, the distance between the rod 26 and fastener 20 can be adjusted through a range which corresponds to the distance by which the length of the opening 38 exceeds the diameter of the outer end portion 40 of the fastener 20. Thus, the rod 26 and a fastener 20 can be moved a relatively large distance apart, as shown in FIG. 5. When this is done, the outer end portion 40 of the fastener 20 will be disposed toward the left (as viewed in FIG. 5) end of the oblong opening 38.

Similarly, the distance between the rod 26 and fastener 20 can be made relatively small as shown in FIG. 6. When this is done, the fastener will be disposed at the right (as viewed in FIG. 6) end portion of the oblong opening 38. Of course, the fastener 20 could be positioned at any location between the left and right ends of the oblong opening 38 to obtain the desired spacing between the fastener and the rod 26.

Once the fastener 20 and rod 26 have been located at a desired spatial relationship relative to each other, the clamp nuts 52 are tightened to hold the rod 26 and fastener 20 in the desired spatial relationship. Thus, if a relatively large distance wa desired between the rod 26 and fastener 20, as shown in FIG. 5, the clamp nut 52 would be tightened with the fastener toward the left (as viewed in FIG. 5) end portion of the oblong opening 38. Similarly, if a relatively small distance was desired between the rod 26 and fastener 20, the clamp nut 52 would be tightened with the fastener disposed at the right end portion of the opening 38 as shown in FIG. 6.

Once the clamp nuts 52 have been tightened to securely hold the connector members 32 against movement relative to the fasteners 20, the set screws 46 are tightened to clamp the connector member 32 against movement relative to the rod 26. Tightening the set screw 46 firmly presses the rod 26 into the relatively small diameter portion 78 of the first embodiment of the connector member 32 (FIG. 4) of the generally oval opening 36 in the manner shown in FIGS. 5 and 6. This results in the connector member 32 being firmly clamped against movement relative to the rod 26. If the second embodiment of the connector member 32 is being used tightening of the set screw 46 firmly presses the rod 26 against the axially spaced arcuate surfaces 120.

In an alternative mounting method, the rod 26 is rotated to simultaneously move one or more vertebrae relative to other vertebrae. In the alternative mounting method, the fasteners 20 are connected with the vertebra 16, in the manner illustrated in FIG. 3. The connector members 32 are then placed in engagement with the rod 26 and fasteners 20 in the manner previously described.

To move one or more of the vertebrae 16 relative to the other vertebrae in the spinal column, the clamp nuts 52 associated with the vertebrae to be moved are tightened to hold the connector member 32 against movement relative to the fasteners in the vertebrae to be moved. The clamp nuts associated with fasteners in other vertebrae of the spinal column 10 are only very loosely tightened. One of the rods 26 is then gripped with a wrench, pliers, or similar device and rotated about an axis which extends through a portion of the rod.

Due to the curved or nonlinear configuration of the rod 26 or portions of the rod, rotating the rod about an axis which extends through a portion of the rod results in other portions of the rod being displaced with a cam action. The portion of the rod which is displaced with the cam action is associated with one or more connector members 32 which have been secured by tightening of the clamp nuts 52 with fasteners 20 in the vertebrae 16 to be moved. Therefore, rotation of the rod 26 applies a sidewards force to these connector members 32 and fasteners 20 to shift one or more of the vertebrae 16 relative to other vertebrae in the spinal column 10.

Once the vertebrae 16 in the spinal column 10 have been moved to their desired spatial relationship, the clamp nuts 52 are tightened to hold the vertebrae in place. It is contemplated that it may be necessary to loosen the clamp nuts 52 for the vertebrae which were shifted by rotation of the rod 26 to provide a fine adjustment to the position of the vertebrae relative to the rod.

Conclusion

The present invention provides a new and improved apparatus and method for use in retaining spinal and/or pelvic elements, such as vertebrae, in a desired spatial relationship. The apparatus includes a fastener 20 having a threaded end portion 22 which engages an element, such as a vertebra in the spinal column 10. A connector assembly 30 interconnects the fastener 20 and a rod 26 which extends along the spinal column 10. The connector assembly 30 is adjustable to enable the distance between the rod 26 and the fastener 20 to be varied while the fastener remains stationary relative to the vertebra 16 to which it is connected.

To accommodate the adjustment between the rod 26 and fasteners 20, an oblong opening 38 is formed in a connector member 32 which interconnects the rod and fastener. Thus, after the connector member 32 has been placed in engagement with both the rod 26 and the fastener 20, the rod and fastener can be moved relative to each other while the connector member is maintained in engagement with both the rod and the fastener. In one specific embodiment of the invention, the oblong opening 38 which accommodates the relative movement between the rod 26 and fastener 20 is engaged by the fastener. Therefore, the connector member 32 and rod 26 can be moved together relative to the fastener 20. If desired, the positions of the vertebrae 16 can be readily adjusted relative to each other by rotating the rod 26 relative to the connector members 32 with the connector members disposed in relatively loose engagement with the rod and fasteners 20 and either none, one or more connector members in relatively tight engagement with a fastener or fasteners.

In another embodiment of the present invention the oblong opening 38 tapers from a first side 100 of the connector member 32 to a second side 102 of the connector member. A pair of identical tapered washers 110 and 112 engage on opposite sides of the connector member 32. Each of the washers 110, 112 has a first side surface 114 and a second side surface 116 extending at an angle to the first side surface. The tapered opening 38 and the tapered washers 110, 112 enable the fastener 20 to be positioned with the axis of the fastener at an angle to the longitudinal axis of the oblong opening. The angle between the axis of the fastener 20 and the longitudinal axis of the oblong opening 38 can be changed by replacing the washers 110, 112 with washers that taper at a different angle.

It should be apparent to those skilled in the art that certain modifications, changes and adaptations may be made in the present invention and that it is intended to cover all such modifications, changes and adaptations coming within the scope of the appended claims.

Having described the invention, the following is claimed:

1. An apparatus for use in retaining spinal elements in a desired spatial relationship, said apparatus comprising a fastener having a first end portion with thread means for engaging a spinal element and a second end portion, a longitudinal member which is positionable along the spinal column, and connector means for interconnecting said longitudinal member and said fastener, said connector means including a connector member having first surface means for defining a first opening through which said longitudinal member extends, said first opening having a central axis which extends along at least a portion of said longitudinal member, first clamp means for holding said longitudinal member and connector member against movement relative to each other, said connector member having second surface means for defining an oblong second opening through which said second end portion of said fastener extends, said oblong second opening having a longitudinal axis extending perpendicular to the central axis of said first opening, said connector member being movable relative to said fastener through a range of movement along the longitudinal axis of said oblong second opening, means for positioning said fastener with the axis of said fastener at an angle to the longitudinal axis of said oblong second opening, and second clamp means for holding said fastener and connector member against movement relative to each other.

2. An apparatus as set forth in claim 1 wherein said means for positioning said fastener with the axis of said fastener at an angle to the axis of said second oblong opening includes a pair of identical washers through which said fastener extends, each of said washers including a first side surface and second side surface extending at an angle to said first side surface.

3. An apparatus for use in retaining spinal elements in a desired spatial relationship, said apparatus comprising:
   a fastener having a threaded end portion for engaging a spinal element;
   a longitudinal member positionable along the spinal column;
   a connector member for interconnecting said fastener and said longitudinal member, said connector member including a mounting section with surface means for defining an oblong opening through which said fastener extends, the oblong opening enabling the distance between said fastener and said longitudinal member to be varied; and
   a pair of identical washers through which said fastener extends, said washers engaging on opposite sides of said mounting section, each of said washers having a first side surface and a second side surface extending at an angle to said first side surface.

4. An apparatus as set forth in claim 3 wherein the opening in said mounting section tapers from one side of said mounting section to the other side of said mounting section.

5. An apparatus as set forth in claim 3 further including a nut engageable with said fastener to clamp said washers and said fastener to said connector member.

* * * * *